US006758964B2

(12) United States Patent
Roudil et al.

(10) Patent No.: US 6,758,964 B2
(45) Date of Patent: Jul. 6, 2004

(54) DEVICE FOR SEPARATING PHASES OF A DIPHASIC MIXTURE AND ITS APPLICATION TO THE DETERMINATION OF THE PHYSICAL AND/OR CHEMICAL PARAMETERS OF THIS MIXTURE

(75) Inventors: Danielle Roudil, Tresques (FR); Francis Malzieu, Piolenc (FR)

(73) Assignee: Commissariat a l'Energie Atomique, Paris (FR)

(*) Notice: Subject to any disclaimer, the term of this patent is extended or adjusted under 35 U.S.C. 154(b) by 47 days.

(21) Appl. No.: 10/201,138

(22) Filed: Jul. 24, 2002

(65) Prior Publication Data

US 2003/0057150 A1 Mar. 27, 2003

(30) Foreign Application Priority Data

Jul. 25, 2001 (FR) .......................................... 2001 09923

(51) Int. Cl.[7] ........................ B01D 11/04; B01D 17/032
(52) U.S. Cl. ........................ 210/85; 210/96.1; 210/299; 210/511; 137/173; 422/256; 73/61.59; 73/863.21
(58) Field of Search ........................... 700/273; 702/25; 210/85, 96.1, 299, 511; 137/173; 422/256; 73/61.59, 863.21

(56) References Cited

U.S. PATENT DOCUMENTS

| 4,405,988 A | * | 9/1983 | Forster et al. ............... 700/273 |
| 4,430,301 A | * | 2/1984 | Evers ........................... 210/511 |
| 4,647,371 A |   | 3/1987 | Schmitt et al. |
| 4,726,221 A |   | 2/1988 | Tavlarides et al. |
| 6,015,494 A |   | 1/2000 | Siverling et al. |

FOREIGN PATENT DOCUMENTS

| EP | 0 035 936 | 9/1981 |
| EP | 0 551 162 | 7/1993 |
| FR | 790 656 | 11/1935 |
| FR | 2 478 314 | 9/1981 |
| FR | 2 780 789 | 1/2000 |
| GB | 645 710 | 11/1950 |

OTHER PUBLICATIONS

Jongheop Yi, et al., Ind. Eng. Che. Res., vol. 29, No. 3, pp. 475–482, "Model for Hold–Up Measurements in Liquid Dispersions Using an Ultrasonic Technique", 1990.
C. Tsouris, et al., Chemical Engineering Science, vol. 46, No. 11, pp. 2857–2865, "Control of Dispersed–Phase Volume Fraction in Multistage Extraction Columns", 1991.

* cited by examiner

Primary Examiner—Terry K. Cecil
(74) Attorney, Agent, or Firm—Oblon, Spivak, McClelland, Maier & Neustadt, P.C.

(57) ABSTRACT

A device for separating and renewing phases of a diphasic liquid—liquid mixture, in which a first liquid phase and a second liquid phase are circulated in counter current in a liquid—liquid extraction device. The device is in the form of a straight hollow cylinder with one of the bases being either the wall of the device or being in contact with the wall of the device. The device also includes an input orifice for the phase the user wishes to trap, an output orifice that is smaller than the input orifice for the phase that the user wishes to trap, separated, and a third orifice of an intermediate size when compared to the size of the input and output orifices for evacuating a non-desired phase.

18 Claims, 6 Drawing Sheets

DEVICE FOR SEPARATING PHASES OF A DIPHASIC MIXTURE AND ITS APPLICATION TO THE DETERMINATION OF THE PHYSICAL AND/OR CHEMICAL PARAMETERS OF THIS MIXTURE

DESCRIPTION

The invention relates to a device for separating phases of a diphasic mixture and the application of this device to the determination of the physical and/or chemical parameters of a diphasic mixture, in particular a liquid—liquid diphasic mixture, preferably a liquid—liquid diphasic emulsion.

In particular, the invention enables the physical parameters of a diphasic mixture, such as a diphasic emulsion, to be determined by propagation of plane sound waves.

Within the scope of the present invention, diphasic mixture is generally understood to mean any emulsion or dispersion in which a first phase, for example a solution, is in the form of a continuous phase, and a second phase, for example a solid, liquid or gas phase, is in the form, for example, of droplets or particles dispersed in the continuous phase. The second phase is usually called "dispersed phase".

This type of diphasic mixture is used in particular to separate chemical elements in solution. The separation process essentially consists in bringing into contact a first solution, for example an aqueous solution, containing chemical elements, with a second solution comprising, for example, an organic solvent, which plays the role of an extractant. This bringing into contact is intended to allow a transfer of material between the two solutions.

The transfer of material is favoured by the formation of a diphasic mixture in the form of an emulsion or dispersion with fine droplets, in such a way as to increase the interfacial exchange area between the phases present. Decantation then allows the liquids to be separated after the transfer of the material.

Different separation devices that operate according to the process mentioned above are known. Among these, mixer decanter type devices, centrifuge extractor type devices or pulsed column type devices may be cited.

In extraction columns, two liquid phases are made to circulate in counter-current, wherein the heavy phase is injected into the top of the body and the light phase is injected into the bottom of this body. By bringing these two phases into contact, the element to be separated is shared out between each of the phases according to the laws of chemical thermodynamics and, by playing on the affinity of an element for one of the phases, one can extract this element almost completely and separate it from other elements.

Thus, in particular, liquid—liquid extraction processes, used in reprocessing of used fuel operations, are carried out in contactors that, in their mixing zone, produce diphasic emulsions. The efficiency of the transfer of elements between phases is particularly linked to the local volume percent of the dispersed phase and the local interfacial exchange area, but one also seeks to determine other physical and chemical parameters of liquid phases present in the emulsion zone, such as elementary concentrations of elements (for example U, Pu), conductivity, acidity, density, etc.

These various parameters may be determined by several procedures. The first procedure consists in taking a sample, in other words a small volume of emulsion, and carrying out measurements on each phase after leaving them to decant.

However, this type of procedure has disadvantages. In fact, taking a sample of emulsion disrupts the hydraulic operation of the contactor.

Moreover, sampling is only possible if the separation device contains a sufficient volume of mixture. Furthermore, the sampled volume must be re-injected into the separation device or must be stored after each measurement. In addition, in the event where the diphasic mixture contains very radioactive substances, the sampling and the storage of measurement samples may be impracticable or very restricting.

A second procedure, intended in particular to establish the density of the continuous phase and the velocities or propagation times of the waves separately in each of the phases during processing, consists in installing, in the separation device, decantation chambers, near to a mixing zone. These "in situ" decantation chambers are however likely to modify the hydraulic behaviour of the device and to locally modify the characteristics of the diphasic mixture.

More precisely, as regards more specifically the local retention rate, a method for measuring the local retention rate by ultrasound wave propagation has already been described in documents (1), (2) and (3).

It shows that this parameter $\beta$ may be represented by:

$$\beta = \frac{t - t_c}{g_d t_d - g_c t_c} \quad (1)$$

wherein:

$t$, $t_c$ and $t_d$=time of flight of the ultrasonic wave in the emulsion, the continuous phase and the dispersed phase alone; and $g_c$ and $g_d$=correction factor for the acoustic path in the aqueous and organic phases.

When transfer of material between the phases occurs, an on-line calibration of the propagation velocities in each of the phases must be carried out under the same physical and chemical conditions as in the measurement in the emulsion.

A destructive method has been proposed in document (4) by sampling and decanting a volume of emulsion before measurement.

An acoustic microscopy method has also been described in document (5) and has the advantage of being neither destructive nor intrusive, but it only allows one to determine the calibration parameter in the continuous phase.

Similarly, as regards the interfacial exchange area, there are optical methods for analysing the average size and the average number of droplets allowing the local interfacial exchange area to be determined. However, these techniques, by light diffusion and diffraction, assume that the local retention rate on-line is known; it is, for example, the principle on which are based the devices of the FORULACTION® Company, sold under the name TURBISCAN®.

The large amount of droplets does not allow simple determination, by analysis and image processing, to be conceived.

On-line determinations of other parameters are achieved through analyses on samples taken.

The measurement of the density of the continuous phase is achieved in document (5) by acoustic microscopy, but the method on its own does not allow the value in the dispersed phase to be determined.

The problem of determining the physical and chemical parameters is particularly acute in the devices presently used in new liquid—liquid extraction installations for the reprocessing of used nuclear fuels. In fact, in order to limit the volumes of nuclear material, the columns are very small.

In such devices, few samples may be taken on-line and the geometry of the extraction devices implies limiting, as much as possible, hydraulic disruptions by intrusion or local modification of the dimensions.

There is therefore a need for a device for separating and renewing the phases of a diphasic mixture, in particular a liquid—liquid diphasic mixture, for example a liquid—liquid diphasic emulsion, which does not modify the hydraulic behaviour of the device in which it is placed and which does not modify the characteristics of the diphasic mixture.

There is also a need for a device for separating and renewing the phases of a diphasic mixture, in particular a liquid—liquid diphasic mixture, which allows perfect, complete separation and renewal of the phases.

There is also a need for a device for measuring the physical and chemical parameters of a liquid—liquid diphasic emulsion, which allows these measurements to be made without taking samples, without intrusion, without inducing hydraulic disruptions and without modifying the characteristics of the diphasic mixture.

Finally, there is a need for a measurement device that allows such measurements to be made with a high degree of reliability and precision, whatever the nature and the volume of the emulsion.

The aim of the present invention is to provide a device for separating and renewing the phases of a diphasic mixture, for example a liquid—liquid diphasic emulsion, which meets, among others, the requirements cited above.

The aim of the present invention is also to provide a device for separating and renewing the phases of a diphasic mixture, for example a liquid—liquid diphasic emulsion, which does not have the drawbacks, limitations, defects and disadvantages of devices of the prior art and which solves the problems of the prior art.

This aim and others are attained, in accordance with the invention, by a device for separating and renewing the phases of a liquid—liquid diphasic mixture, comprising a first liquid phase and a second liquid phase circulating in counter-current in a liquid—liquid extraction device, wherein said separation device is in the form of a straight hollow cylinder, in which the principal generator is substantially perpendicular to the direction of movement of the liquid phases, and in which one of the bases comprises the wall of the extraction device or is positioned in contact with this wall, said cylinder comprising:

An input orifice for the phase that one wishes to trap, placed on the lateral wall of the cylinder, substantially in the axis of movement of said phase that one wishes to trap.

An output orifice for said phase that one wishes to trap, separated, relatively smaller than said input orifice and located on the other cylinder base.

A third orifice, for the other phase, of intermediate size between the size of the input orifice and the size of the output orifice, placed near to the input orifice.

The device for separating and renewing phases according to the invention, due to its specific geometry, the specific lay out of the phase input and output orifices and the relatively specific dimensions of these orifices, has the effect, among other things, of limiting hydraulic disruptions, not affecting the characteristics of the diphasic mixture, and allowing complete, total separation of the phases. As a result, the device according to the invention provides a solution to the problems posed by devices of the prior art and meets, in a satisfactory manner, all of the requirements indicated above.

Preferably, the diphasic mixture is a liquid—liquid diphasic emulsion (or dispersion).

Advantageously, the material making up the device according to the invention has a wettability that is more adapted to the phase that one wishes to trap.

The phase that one wishes to trap is generally either an organic phase or an aqueous phase.

Thus, if the phase that one wishes to trap is an organic phase, a material that is both organophilic and hydrophobic, such as TEFLON® (PTFE, polytetrafluoroethylene), PVDF (poly(vinylidene fluoride)) which better resists radiation), or polychlorotrifluoroethylene (KEL-F®) is preferably selected.

If the phase that one wishes to trap is an aqueous phase, then a hydrophilic material, such as stainless steel or polyethylene, is preferably selected.

Advantageously, the device according to the invention has a small size, and is thus perfectly adapted to the liquid—liquid extraction devices in installations for reprocessing used nuclear fuels.

Despite its small size, it perfectly fulfills its role of separator, while nevertheless retaining sufficient volume of separated phase to allow physical and chemical measurements and analyses to the carried out, for example, on-line.

The size and the dimensions of the device according to the invention are obviously a function of the size of the liquid—liquid extraction device, in which it will be placed.

The length and the diameter of the devices are adjusted in order to:

Maintain the local volume

Ensure a transparency of 20 to 30% (the separators then replace the column packing plates).

The length of the device thus remains generally less than or equal to 85% of the diameter of the body or the flange. The maximum diameter of the device is generally less than or equal to 90% of the diameter of the body or the flange of the extraction device.

It should also be pointed out that the intermediate flange does not necessarily have the same geometry as the body.

The minimum values are the minimum diameter and length values (separation volume) required to ensure separation and renewal.

According to our experience, the minimum length is close to 6 mm, for example ($1_{min}$–6 mm) and the minimum diameter is near to 10 mm, for example ($\varnothing_{min}$–10 mm).

But this also depends on the material used and the nature of the phase. In fact, the "coupling" is more or less important on the internal walls depending on the affinity, viscosity, etc.

Thus, as an example, if the extraction device has a diameter (body diameter) of 50 mm, the device(s) according to the invention will be cylinders with diameter of 25 mm and length of 20 mm.

If the extraction device has a diameter of 27 mm, the device(s) according to the invention will be cylinders with diameter of 15 mm and length of 12 mm.

Finally, if the extraction device has a diameter of 15 mm, the device(s) according to the invention will be cylinders with diameter of 12 mm and length less than 10 mm (exterior 12 mm to 13 mm).

The separation device according to the invention may be fitted with one or several different sensors, to carry out measurements in the separated phase.

These measurements are particularly physical and/or chemical measurements, such as concentration, conductivity, temperature, pH, etc.

In addition, the invention concerns an intermediate instrumentation flange for a liquid—liquid extraction device comprising one or several devices for separating and renewing phases, as described above.

Advantageously, said flange is fitted with one or several sensor(s), for example from one to ten sensors that are sensors that carry out physical/chemical measurements, on-line, in the separated phase of each of the devices for separating and renewing the phases.

Advantageously, said flange is fitted, in addition, with one or several sensor(s), for example from one to ten sensors that are ultrasonic sensors for carrying out measurements within the diphasic mixture itself, for example the emulsion.

The sensor(s) (whether in the separators or independent of these in the flanges or independent of these) carry out physical, chemical, optical, acoustical measurements, selected particularly among density, concentration, acidity, temperature, pH, conductivity, diffusion, diffraction, light absorption and propagation and attenuation of sound wave measurements.

The flange may thus comprise one or several sensor(s) for carrying out reference measurements relating to one or several parameter(s) or order(s) of magnitude in the separated phase of the phase separation device(s) and one or several sensor(s) for carrying out measurements relating to the same parameter(s) or order(s) of magnitude within the emulsion.

The sensor(s) may in particular be ultrasonic sensors.

The flange may advantageously comprise three or four ultrasonic sensors and two phase separation devices.

Finally, the invention concerns an on-line measurement, instrumentation device for a liquid—liquid extraction device comprising one or several flange(s), as defined above.

Advantageously, said flanges are placed along the extraction device, in order to establish a measurement profile concerning one or several parameter(s) of the mixture.

Figure 1:
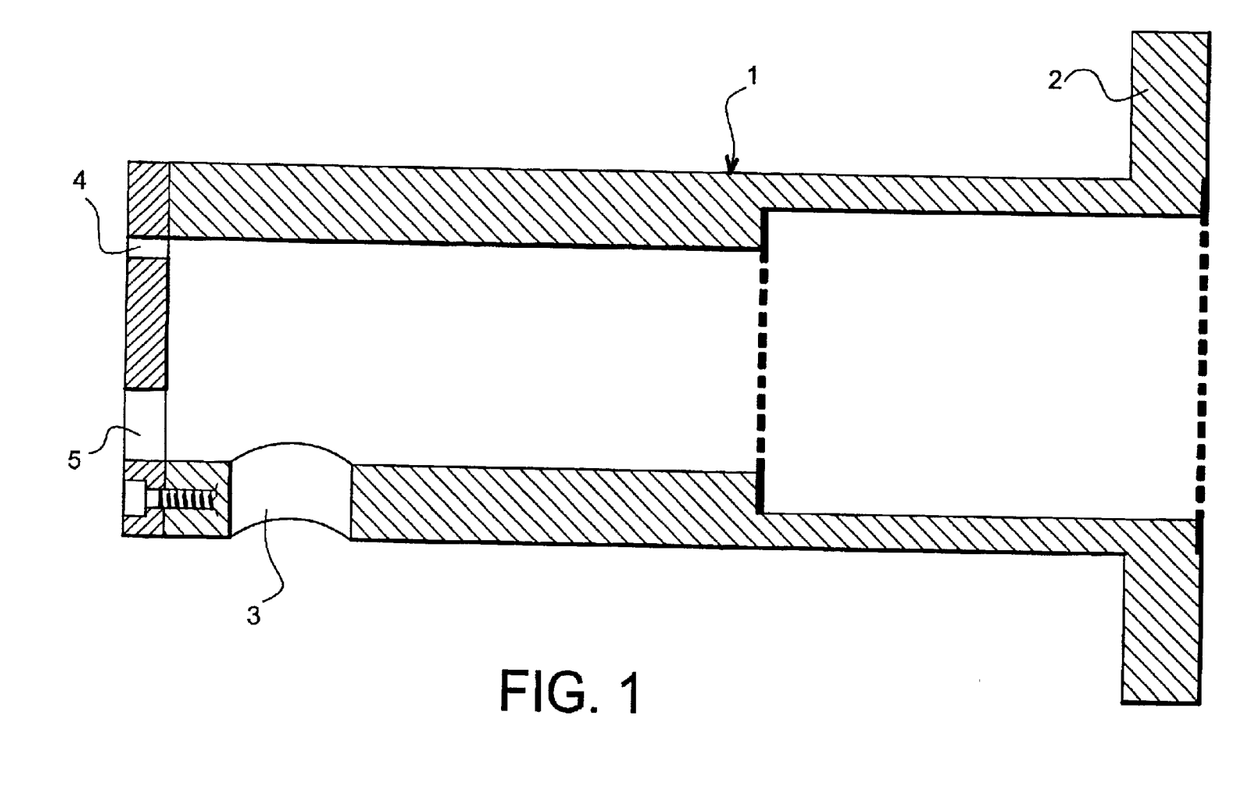
FIG. 1 is a schematic lateral cross-sectional view of a device for separating and renewing phases according to the invention.

The invention will now be described in greater detail in the description that follows, which is given for illustrative purposes and is in nowise limitative, and by referring to the attached drawings, in which:

FIG. 1 is a representation of a device for separating and renewing phases of a diphasic mixture, in particular a liquid—liquid emulsion according to the invention, which enables the automatic separation and renewal of said phases.

This device is in the form of a straight hollow cylinder, in which one of the bases of said straight cylinder comprises the wall (2) of the extraction device or is positioned in contact with said wall.

The cylinder is equipped with phase input and renewal orifices.

In accordance with the invention, the cylinder (1) is placed in the extraction device, in such a way that its principal generator is perpendicular to the direction of movement of the liquid phases.

The input orifice (3) of the phase that one wishes to trap is larger and is generally in the form of a circular drilling or punching with a diameter, for example, of 2 to 5 mm, for a column with a diameter less than 30 mm, the diameter of the drilling is obviously linked to the volume of the separator.

The cylinder also comprises an output orifice for the phase that one wishes to trap (4), which is generally situated on the side in relation to the input orifice, in other words on the other cylinder base, which is not the same base comprising the wall of the extraction device or positioned in contact with this wall. This output orifice is generally in the form of a circular drilling or punching and it is smaller than the input orifice. Thus, this orifice will generally have a diameter, for example, of from 0.8 to 1.2 mm, for a column with a diameter less than 30 mm.

Finally, the separation device according to the invention also comprises a third orifice (5), located near to the input orifice, generally on the same cylinder base as the orifice (4), and which is used for evacuating, if necessary, the non-desired phase, if it penetrates into the device.

Figure 2:
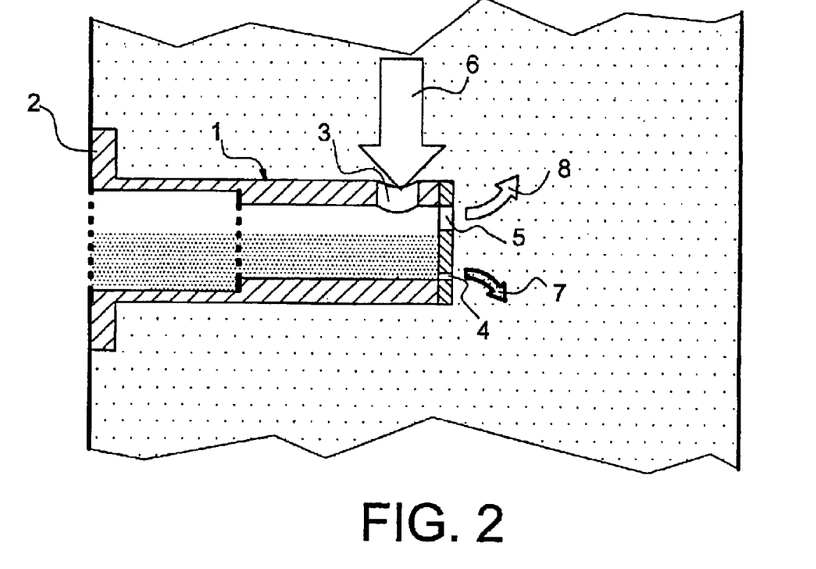
FIG. 2 is a schematic lateral cross-sectional view showing the separation and renewal of an aqueous phase in a separation device according to the invention, where the separator is made out of stainless steel or polyethylene.
Figure 3:
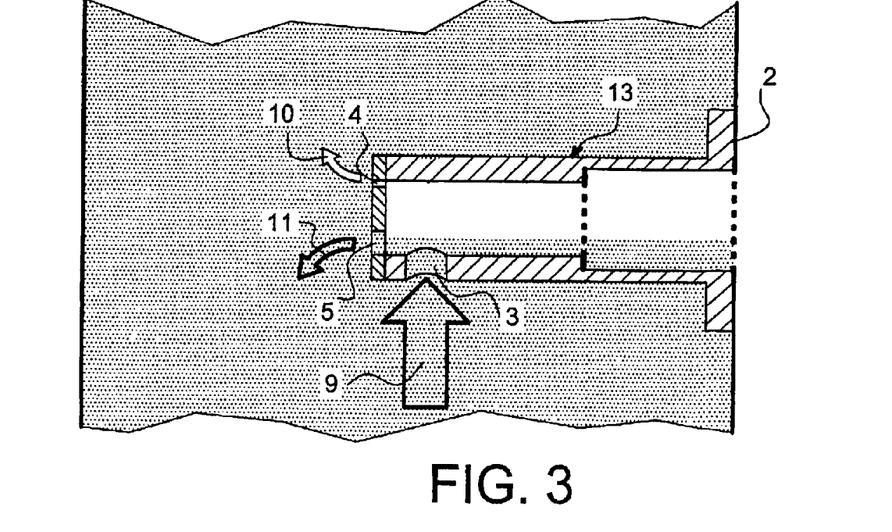
FIG. 3 is a schematic lateral cross-sectional view showing the separation and renewal of an organic phase in a separation device according to the invention, where the separator is made out of TEFLON®.

FIGS. 2 and 3 show the respective mechanisms for separating and renewing a heavy aqueous phase (dispersed in the organic phase) and a light organic phase (dispersed in the aqueous phase).

For example, in FIG. 2, the diphasic mixture (aqueous phase in the organic phase) penetrates (arrow 6) via the orifice (3) into the separation device (1). The separated aqueous phase is evacuated (arrow 7) via the orifice (4), and the organic phase that has penetrated the device is evacuated (arrow 8) via the orifice (5).

In FIG. 3, the diphasic mixture (organic phase in the aqueous phase) similarly penetrates (arrow 9) via the orifice (3) into the separation device (1). The separated organic phase is evacuated (arrow 10) via the orifice (4), and the aqueous phase that has penetrated the device is evacuated (arrow 11) via the orifice (5).

The separation and renewal are carried out in an efficient manner thanks to the appropriate wettability properties of the materials used to make the separators according to the invention, and as a result little emulsion is introduced, and generally only the phase that one wishes to separate appears.

In other words, the materials that make it possible to obtain the separation capabilities of the devices according to the invention are selected as a function of their wettability properties in relation to the nature of the phases of the emulsion. Thus, for example, in reprocessing operations, a hydrophilic material is preferably chosen, such as stainless steel or polyethylene, to separate the aqueous phase made up, for example, of nitric acid; whereas one uses a rather hydrophobic and organophilic material, such as TEFLON®, and certain other polymers resistant to irradiation, to separate the organic phase, made up, for example, of TBP at a concentration of 30% in TPH.

The cylindrical geometry of the separators has shown itself to be optimal in limiting as much as possible the hydraulic disruptions linked to the intrusion or the local modification of dimensions, and moreover, the devices according to the invention adapt perfectly and this is surprising for small volume devices, for example the small diameter columns that are now used in extraction installations for reprocessing used fuels.

The geometry of the devices according to the invention is a function of the dimensions of the device containing the emulsion and the minimum volume of separated phase needed to carry out on-line physical/chemical measurements and analyses.

As an example, in an extraction column comprising a body with a diameter of 50 mm, the devices according to the invention will have a diameter of 25 mm and a length of 20 mm.

In a column comprising a body with a diameter of 27 mm, the devices according to the invention will have a diameter of 15 mm and a length of 12 mm.

In a column comprising a body with a diameter of 15 mm, the devices according to the invention will have a diameter of 12 mm and a length of 10 mm.

Whatever the volume, even if very small, of the device on which are positioned the devices according to the invention, these devices only cause very little hydraulic disruption and ensure excellent separations and renewals of the phases.

Thus, tests on pulsed pilot columns with diameters of 50 and 27 mm have shown that the separation power of the devices according to the invention uniquely depends on the agitation energy, conventionally represented by the result of the amplitude×frequency of the column pulsation.

Curves giving the sound propagation velocity at 20° C. as a function of the pulsation pressure in mbar and the a.f., in other words the result of the amplitude×frequency representing the pulsation energy put into the diphasic system for each pulsed column with different diameter (50 mm and 27 mm) and for each material tested (stainless steel, TEFLON® and polyethylene) were prepared. The separation was proved by the stability of the value of the sound velocity, whatever the quantity of emulsion present locally in the body of the pulsed column.

As for the renewal efficiency, it was validated by the modification of the acidity of the phases introduced. The results showed, by comparison to analyses taken on samples, that it was always fully obtained.

The acoustic propagation velocity at constant temperature was measured and compared with calibrated values obtained in the laboratory. The changes as a function of the acidity were totally comparable.

Moreover, we have been able to demonstrate, in a diphasic system in equilibrium, the operating range of a stainless steel separator in terms of pulsation pressure and the result of amplitude×frequency. For the aqueous phase, in the stainless steel separator, no emulsion was introduced between 0 and 130 mbars, i.e. result of amplitude×frequency a.f$\leq$2.6 cm.s$^{-1}$.

In an analogous manner, for a Teflon® separator, the operating range for the separation of the organic phase was 0$\leq$a.f.<3.5 cm.s$^{-1}$.

Again in an analogous manner, for the polyethylene separator for the aqueous phase, the operating range in a.f. was identical.

Moreover, the renewal efficiency of separators made out of stainless steel, Teflon and polyethylene was proved by showing the variation in the propagation velocity in the separated medium during mass transfer (simulated by variation of acidity).

The velocity variation law, as a function of the acidity, was comparable to that obtained in the laboratory.

Moreover, the invention concerns a device, called an instrumented "intermediate flange", for a liquid—liquid extraction device, such as a pulsed column. Said flange may comprise one or several devices, for example up to ten devices for separating and renewing phases, such as described above.

Figure 4:
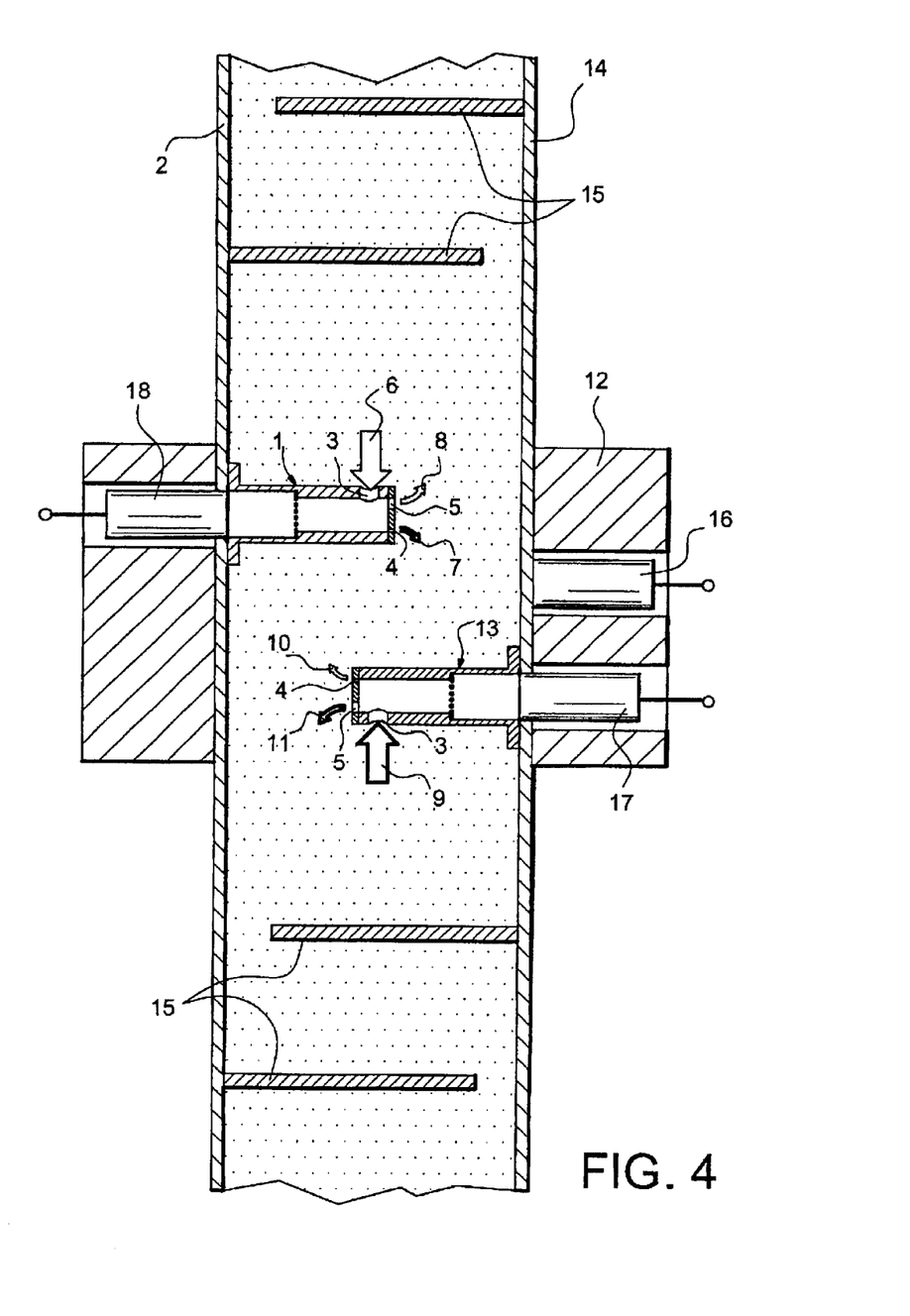
FIG. 4 is a schematic lateral cross-sectional view showing an intermediate flange instrumented and equipped with two phase separators according to the invention, one for the aqueous phase and the other for the organic phase, where said flange is placed in a plate type liquid—liquid extraction column and is fitted with sensors to carry out measurements in each of the separated phases and in the diphasic mixture.

FIG. 4 shows such an intermediate flange (12) equipped with two phase separators (1, 13), one for one of the phases, for example the aqueous phase (1) and the other for the other phase, for example the organic phase (13). Said flange is placed in the liquid—liquid extraction device, such as a pulsed column (14) provided with plates (15).

The sensors (16, 17, 18) are grouped together at the level of the flange, in direct contact, or by transmission via wave guides. Any type of physical, chemical, optical, acoustical measurements, etc., such as the measurement of density, concentration, acidity, conductivity in the emulsion and/or separated phases in each of the separators is conceivable and only leads to a possible modification of the geometry of the separator, in order to position the sensor. Specific and useful sensors are ultrasonic sensors.

The internal geometry of the flange is calculated as a function of the dimensions of the liquid—liquid extraction device, for example a pulsed column, and does not create hydraulic disruptions.

Thus, the volume is maintained, in other words the volume of the flange is equal to the volume of a same height of column body, taking account of the separation devices. In order to avoid too high head losses and the risk of rapid saturation, the transparency is maintained above 20% or 25% at all points.

It should be recalled that the transparency is defined as the ratio of the plate diameter over the column diameter.

The flange may be made out of any material, for example stainless steel, or a polymer, compatible with the phases of the emulsion, which can be machined and is resistant to the chemical attack of the solutions used and compatible, if necessary, with an installation in an irradiated environment.

The flange in FIG. 4 is equipped, for example, with three sensors (16, 17, 18), and preferably these sensors are ultrasonic sensors, in which measurements enable numerous emulsion parameters to be determined, such as the density, the local retention rate, the acoustic impedance, the size and number of droplets, etc.

In FIG. 4, two sensors (17, 18) take measurements in the separated phases of each of the separators, and a third sensor (16) takes measurements in the emulsion.

The three ultrasonic sensors are linked to a multiplier—emitter—amplifier for ultrasonic signals, then a digitising and processing stage for ultrasonic signals.

Thus, this flange enables in particular a measurement of the local retention rate (or density of the dispersed phase) to be performed with self-calibration by phase separation in situ, taking account of the physical/chemical modifications sustained by the phases of the emulsion. According to the formula (1) above, three ultrasonic sensors are required. The parameters $t_c$ and $t_d$ are measurable in the phase separators by temporal localisation of the first echo, knowing the length of the acoustic path 2×1 (where 1 is the length of the separator). The crossing time t in the emulsion may be measured by transparency or by echo, depending on the value of the diameter of the flange and the nature of the phases of the emulsion (sound absorption linked to the viscosity) and the frequency of the selected ultrasounds.

For example, in a nitric acid—TBP 30% in TPH phase system, the measurement by echo can be carried out without any difficulty at 2 MHz, up to a diameter of 20 mm (acoustic path of 40 mm).

Figure 5A:
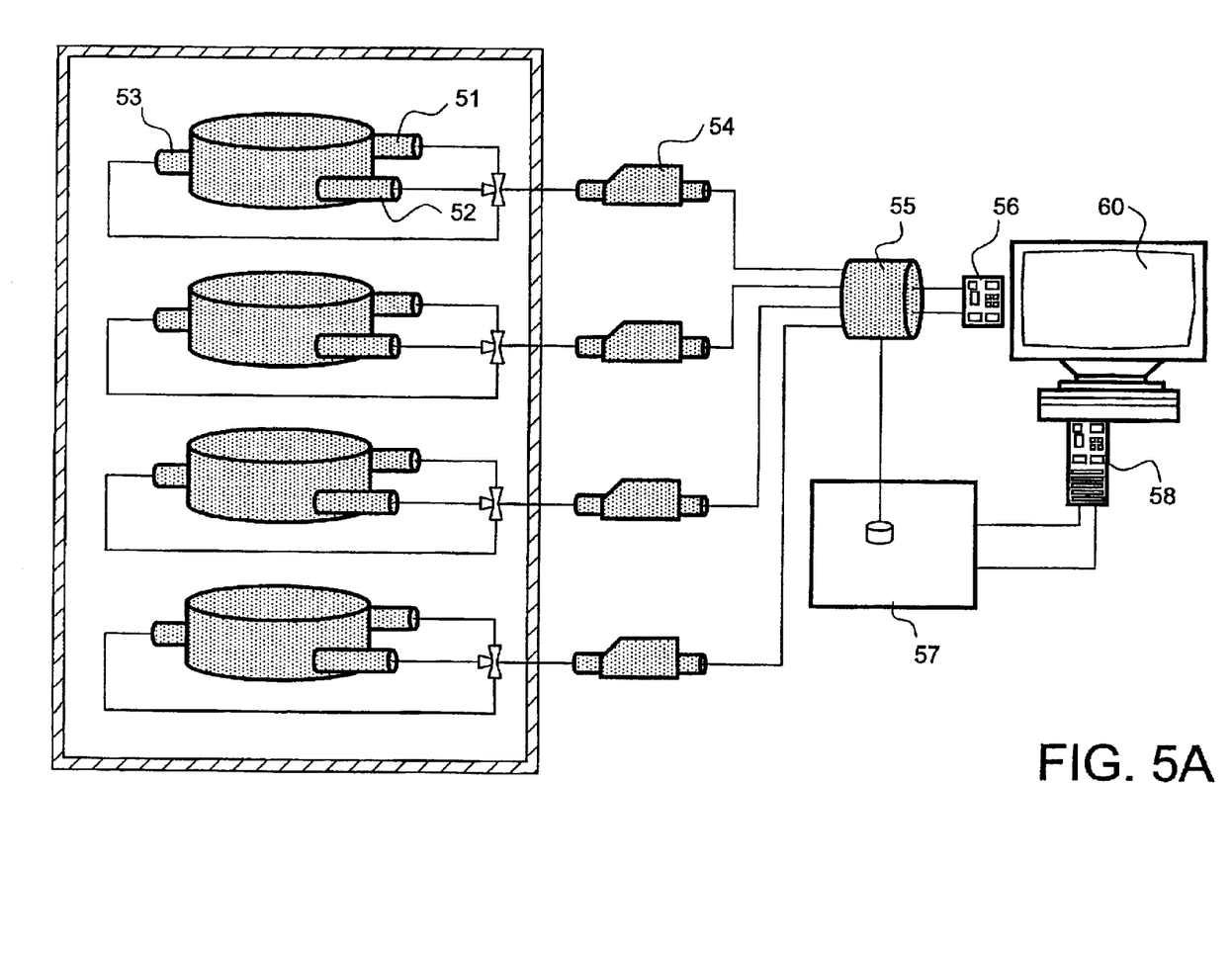
FIGS. 5A and 5B are schematic views showing examples of the carrying out of measurements on several flanges fitted with phase separators, while multiplexing the signals (1 and 2).
Figure 5B:
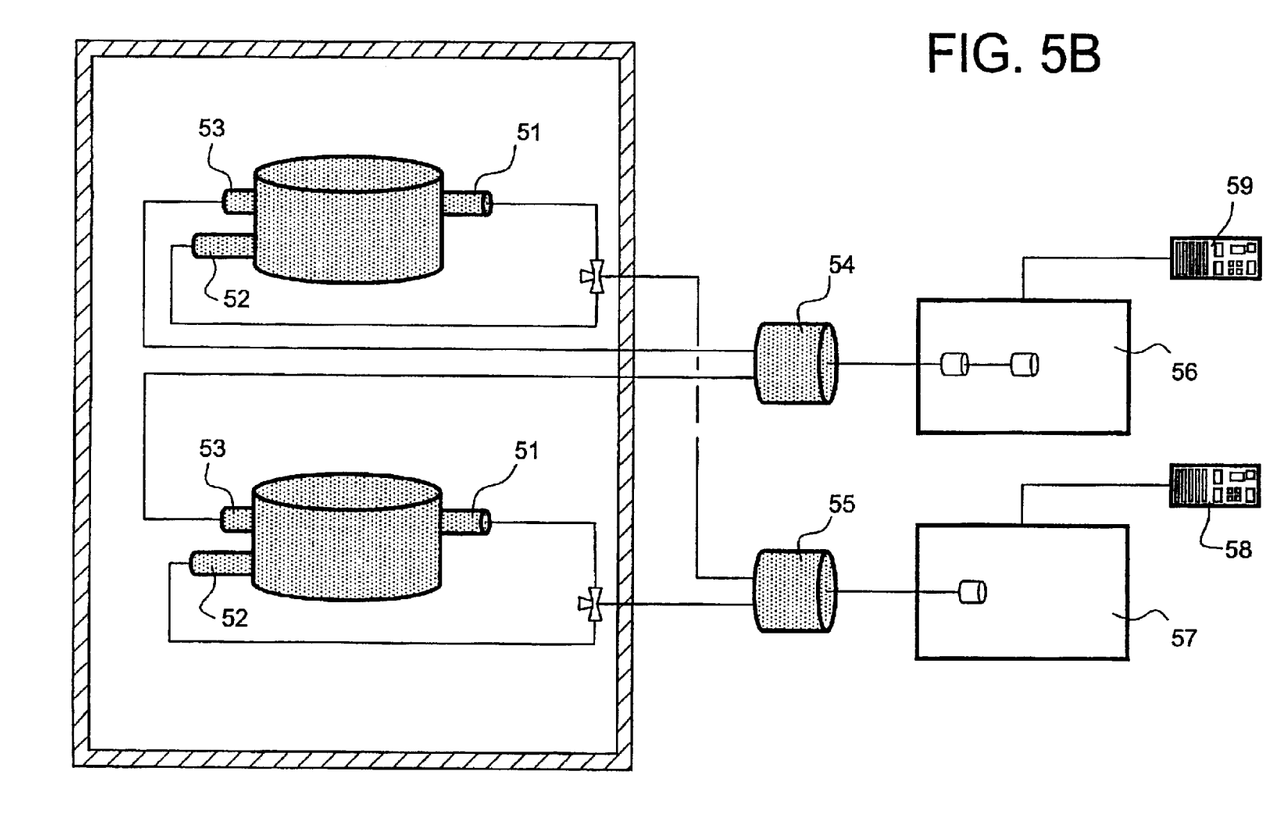

FIGS. 5A and 5B show the two experimental assemblies possible for carrying out this on-line measurement of the local retention rate. The determination of three ultrasonic wave crossing times (localisation of the first echo alternation) may be done by numeric computation or by analogue interface.

In the assembly shown in FIG. 5A, the ultrasonic sensors (51, 52, 53) in a same flange are excited in a synchronous manner. The response is the superimposition of the three echos.

Given that either the propagation media are different or the acoustic pathways are different, the three echos are not superimposed and may easily be decorrelated.

(54) is an intermediate electronic impedance adaptation device. It may include, if necessary, an amplifier.

(55) is a multiplexer that makes it possible to analyse the measurement on several flanges, successively.

(56) is the digital board for controlling the multiplexer.

(57) is an ultrasonic emitter/amplifier.

(58) is a numerical data acquisition board for the processing carried out on the calculator (60).

FIG. 5B shows an example of on-line measurement, on several (2) flanges, of the retention rate, by ultrasound.

The two measurements by the sensors (51) and (52) are carried out, at the same time, in the two separators, in a synchronous manner.

Since the media are different, the echos are temporally separated.

The multiplexer (55) makes it possible to analyse the signals in the phase separators successively on several flanges.

The measurement by the sensor (53) is carried out in the emulsion.

The multiplexer (54) thus makes it possible to examine the measurements in the emulsion in several flanges, successively.

The multiplexers (54) and (55) are controlled in parallel.

(56) and (57) are specific ultrasound emitters/amplifiers.

(58) and (59) designate associated data acquisition boards for the digitisation and processing of data by calculator.

We displayed the on-line retention rate measurement results obtained by pulsed column with a diameter of 27 mm, with phase separators with a length of 10 mm and an acoustic pathway in the emulsion of 16 mm. The acoustic measurements were compared, to the measurements taken on samples. The level of retention was modified by acting on the pulsation pressure.

It can be concluded from this that the absolute difference remains less than two points.

Moreover, the association of measurements in the phase separators and in the emulsion, thanks to the notion of a flange grouping together all of the local instrumentation, makes it possible to carry out new measurements that characterise the emulsion.

Thus, in the separated phases, when the phase separators are made out of polymeric materials, the temporal localisation of the echo and the measurement of its maximum amplitude enables the acoustic impedance of the solution to be determined (obtained from the density multiplied by the sound propagation velocity) and, as a consequence, its density.

In order to take into account the acoustic energy variations emitted from burst to burst, a calibration device must be introduced into the phase separator.

One then determines, from the recording of the average amplitudes on the stem and the bottom disc, assumed to be made out of TEFLON® (same reasoning for other polymers):

$$Z_s = Z_T \cdot \frac{A'_1 \cdot 4 \cdot l \cdot L - A_2 \cdot (\pi d^2 - 4 \cdot l \cdot L)}{A'_1 \cdot 4 \cdot l \cdot L + A_2 \cdot (\pi d^2 - 4 \cdot l \cdot L)}$$

Where:

$Z_S$ and $Z_T$=acoustic impedances of the solution and the TEFLON® (or bottom disc).

$A'_1$ and $A_2$=amplitude of the echos on the standard and bottom.

L and l=dimensions of the standard reflector made out of stainless steel.

d=diameter of the ultrasonic beam.

And the density $\rho$ is then deduced from the equation:

$$\rho = \frac{Z_s}{v}$$

where:

v=acoustic propagation velocity in the solution.

Validation tests on a 50 mm column showed very good determination of the density of nitric acid, with an accuracy of around 0.4%.

In the aqueous phase separator, the standard stem, with high acoustic impedance, may be made out of stainless steel.

In the organic phase separator, the standard stem must have high acoustic impedance and be hydrophobic. It is therefore made out of, for example, glass that has been rendered hydrophobic.

Moreover, the association of the measurement of the retention rate and the acoustic impedance measurements in each separated phase of the emulsion, enables a device for characterising the emulsion also in terms of average size and average number of droplets to be created.

If one considers in fact that a droplet with a size bigger than the acoustic wavelength provokes an attenuation $A_g$ in the signal, then the amplitude of the transmitted signal may be represented by:

$$A_n = A_0 \cdot (A_g)^n$$

Where:

$A_0$=amplitude of the signal without droplets (zero retention rate)

N=number of droplets with the same average diameter d.

It can be shown that:

$$A_G = \frac{4 \cdot Z_{orga}^2}{Z_{aq} + Z_{orga}}$$

where $Z_{aq}$ and $Z_{orga}$ represent the acoustic impedances of the two phases of the emulsion.

Knowing the value of the acoustic measurement of the retention rate and knowing that by definition:

$$\beta = \frac{N \cdot 4/3 \cdot d^3/8}{(\Phi_{US}^2/4) \cdot l}$$

where $\Phi_{US}$ and l=diameter and length of the ultrasonic beam.

One determines an average number N of droplets after estimation of the equivalent number n of droplets of the size of the ultrasonic beam by:

$$N\pi.d^2 = n/2.\pi.\Phi_{US}^2 \text{ and } N = (n^3.\Phi_{US}^2)/(18.l^2.\beta^2)$$

And an associated average diameter:

$$d = \infty \sqrt{(n/2N) \cdot \Phi_{US}}$$

In other words, an interfacial exchange area of $$A = n\pi D^2.$$

The tests carried out in this way on a pulsed column with a diameter of 27 mm clearly showed an attenuation of the signal that changed with the pulsation energy and thus the number of droplets. The acoustic path in the emulsion was 16.4 mm (twice 8.2 mm) in echo on a TEFLON® disc.

The application of the previous formulae give the following summary table.

TABLE 1

| Retention rate | An/A0 | n | N | d | A |
|---|---|---|---|---|---|
| 7.6% | 0.883 | 0.7 | 1.8 | 2.6 mm | 38.2 mm$^2$ |
| 8.8% | 0.715 | 1.9 | 27.5 | 1.1 mm | 104.5 mm$^2$ |
| 15.1% | 0.528 | 3.7 | 64 | 1.01 mm | 205 mm$^2$ |
| 18.3% | 0.502 | 3.95 | 54.8 | 1.14 mm | 223.6 mm$^2$ |
| 21.6% | 0.451 | 4.57 | 60.8 | 1.16 mm | 257 mm$^2$ |

The estimation, from photos, of the average size of the droplets is around 1 to 1.5 mm, at a pulsation pressure of around 100 mbars (retention rate of 15 to 18%)

We have therefore demonstrated that the intermediate flange, instrumented, for example, with three (or four) ultrasonic sensors and equipped, for example, with two phase separators, is an excellent device for the local physical characterisation of a diphasic emulsion, in terms of:

percentage volume acoustic impedance and density average size and number of droplets.

But other physical/chemical parameters may be monitored by the introduction of detectors or sensors in the phase separation zone. In particular, the following are conceivable:

optical fibres for measuring elementary concentrations by UV-visible absorptiometry (spectrophotometry).

conductivity or pH probes.

The principle is to introduce the sensitive element, or a transmission guide, into the separated volume through the walls of the separator. The geometry is adapted to separate the different measurement zones if necessary in order to avoid interactions between them.

Figure 6:
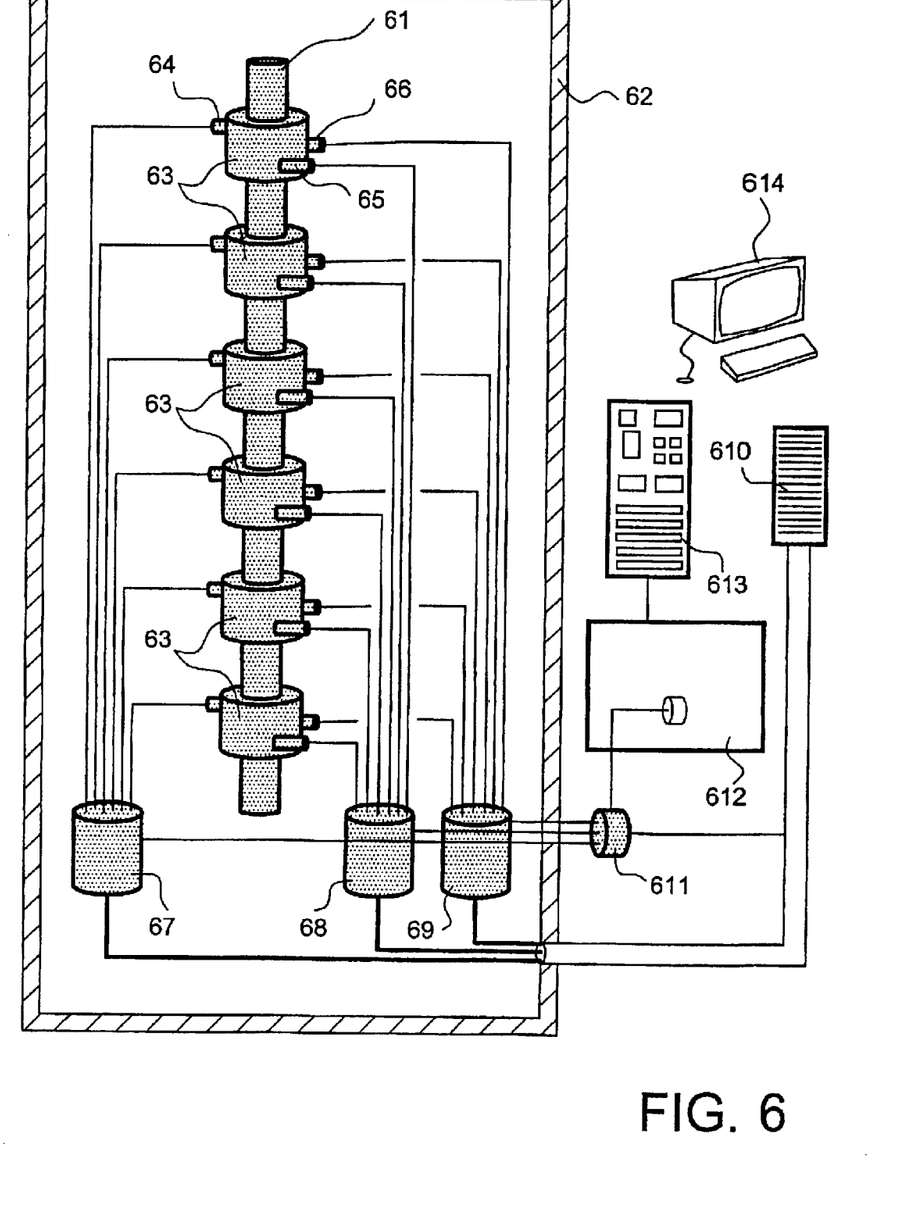
FIG. 6 is a schematic view of a device containing a diphasic mixture, such as an emulsion, along which is placed intermediate instrumented flanges according to the invention, allowing measurement profiles to be established along the mixture zone.

FIG. 6 shows a device containing a diphasic mixture, such as an emulsion, for example a device, such as a pulsed column (61).

Due to the fact that this device may be used to process, for example, radioactive substances, it is preferably reinforced in a leaktight enclosure (62). Said column is fitted with several intermediate instrumented flanges (63) according to the invention. In FIG. 5, six flanges are shown and each is fitted with devices for separating and renewing the phases and sensors, for example ultrasonic sensors.

FIG. 6 thus shows a pulsed column (61) equipped, along the body, with intermediate instrumented flanges (63). They are equipped with three identical ultrasonic sensors (64, 65, 66), each of which carries out a propagation velocity measurement within the three following media:

(1): separated aqueous phase
(2): separated organic phase
(3): emulsion.

We propose here a solution for measuring on-line the profile of the retention rate, while limiting the number of control devices. Several multiplexing systems are used:

all of the sensors (one per flange) taking measurements in the aqueous phase separators are connected to the same multiplexer (67)

all of the sensors (one per flange) taking measurements in the organic phase separators are connected to a second multiplexer (68)

similarly, all of the sensors taking measurements in the emulsion are connected to a third multiplexer (69)

These three multiplexers (67, 68, 69) may then either be controlled directly by a calculator (614) via three specific ultrasonic emitter amplifiers, or as shown in FIG. 6, be connected to an additional multiplexing stage (611), which makes it possible to reduce to a single emitter amplifier (612) and a data acquisition board (613) the measurement chain connected to the control calculator. The reference (610) is a standard numeric input/output board for controlling the multiplexers.

At each instant t, the three multiplexers (67, 68, 69) are commuted on the same channel number and thus ensure the transmission of measurements at the level of a same flange. The additional multiplexer (611) makes it possible to transmit sequentially to the data acquisition board (613), the three echos supplied by the three sensors on the flange. The multiplexers are then commuted onto the following flange, after editing and processing the data acquired by the calculator.

REFERENCES (1) FR-A-2 780 789
(2) U.S. Pat. No. 4,726,221
(3) "Model for hold-up measurements in liquid dispersions using an ultrasonic technique", J. YI and L. L. TAVLARIDES, Ind. Eng. Chem. Res., vol. 29, no. 3, p. 475–482, 1990.
(4) "Control of dispersed-phase volume fraction in multi-stage extraction columns", C. TSOURIS and L. L. TAVLARIDES, Chemical Engineering Science, vol. 46, no 11, p. 2 857–2 865, 1991.
(5) FR-A-2 478 314
(6) EP-A-0 035 936

What is claimed is:

1. A separation device for separating and renewing the phases of a liquid—liquid diphasic mixture, comprising a first liquid phase and a second liquid phase circulating in counter-current in a liquid—liquid extraction device, wherein said separation device is in the form of a straight hollow cylinder, in which a principal generator is substantially perpendicular to the direction of movement of the liquid phases, and in which one cylinder base comprises a wall of the extraction device or is positioned in contact with said wall, said cylinder comprising:

an input orifice for the phase that one wishes to trap, the input orifice being on a lateral wall of the cylinder, substantially in the axis of movement of said phase that one wishes to trap;

an output orifice for said phase that one wishes to trap, the output orifice being separate from and relatively smaller than said input orifice and located on a second cylinder base opposed to the one cylinder base;

a third orifice configured to evacuate a non-desired phase, the third orifice being of intermediate size between the size of the input orifice and the size of the output orifice and being placed near to the input orifice.

2. A separation device according to claim 1, in which said diphasic mixture is a liquid—liquid diphasic emulsion or dispersion.

3. A separation device according to claim 1, made out of a material whose wettability is adapted to the phase that one wishes to trap.

4. A separation device according to any of claims 1 to 3, in which the phase that one wishes to trap is an aqueous phase.

5. A separation device according to any of claims 1 to 3, in which the phase that one wishes to trap is an organic phase.

6. A separation device according to claim 4, made out of a hydrophilic material, including stainless steel or polyethylene.

7. A separation device according to claim 5, made out of a hydrophobic and organophilic material, including polytetrafluoroethylene (TEFLON®), PVDF or polychlorotrifluoroethylene.

8. A separation device according to claim 1, in which the liquid—liquid extraction device is cylindrical, the diameter of the separation device is less than or equal to 90% of the diameter of the liquid—liquid extraction device, and the length of the separation device is less than or equal to 85% of the diameter of the liquid—liquid extraction device.

9. A separation device according to claim 1, fitted with one or several sensors to carry out measurements in the separated phase.

10. Intermediate instrumentation flange for a liquid—liquid extraction device comprising one or several separation devices according to claim 1.

11. Intermediate instrumentation flange according to claim 10, fitted with one or several sensors for carrying out on-line physical/chemical measurements in the separated phase of the separation devices.

12. Intermediate instrumentation flange according to claim 11, fitted, in addition, with one or several sensors for carrying out measurements within the diphasic mixture itself, such as an emulsion.

13. Intermediate instrumentation flange according to claim 11, in which the one or several sensors carry out physical, chemical, optical, or acoustical measurements, and wherein said measurements are selected from a group consisting of density, concentration, acidity, temperature, pH, conductivity, diffusion, diffraction, light absorption, and propagation and attenuation of sound wave measurements.

14. Intermediate instrumentation flange according to claim 10, comprising one or several sensors for carrying out reference measurements relating to one or several parameters in the separated phase of the separation devices and one or several sensors for carrying out measurements relating to the same parameters within the diphasic mixture.

15. Intermediate instrumentation flange according to claim 11, in which said sensors are ultrasonic sensors.

16. Intermediate instrumentation flange according to claim 15, comprising two or three ultrasonic sensors and two phase separation devices.

17. On-line instrumentation device comprising one or several intermediate instrumentation flanges according to claim 10.

18. On-line instrumentation device according to claim 17, in which said one or several intermediate instrumentation flanges are placed along the liquid—liquid extraction device, in order to obtain a measurement profile.

* * * * *